US00PP22972P3

(12) United States Plant Patent
Austin

(10) Patent No.: US PP22,972 P3
(45) Date of Patent: Aug. 21, 2012

(54) ***ROSA HYBRIDA* SHRUB PLANT NAMED 'AUSTOBIAS'**

(50) Latin Name: *Rosa hybrida*
Varietal Denomination: AUStobias

(75) Inventor: David C. H. Austin, Wolverhampton (GB)

(73) Assignee: David Austin Roses Ltd, Albrighton, Wolverhampton (GB)

( * ) Notice: Subject to any disclaimer, the term of this patent is extended or adjusted under 35 U.S.C. 154(b) by 22 days.

(21) Appl. No.: 13/065,148

(22) Filed: Mar. 14, 2011

(65) Prior Publication Data

US 2012/0096604 P1 Apr. 19, 2012

(30) Foreign Application Priority Data

Oct. 13, 2010 (QZ) ..... PBR 20102155

(51) Int. Cl.
*A01H 5/00* (2006.01)

(52) U.S. Cl. ..... Plt./107; Plt./102

(58) Field of Classification Search ..... Plt./102, Plt./107

See application file for complete search history.

*Primary Examiner* — Susan McCormick Edwoldt

(74) *Attorney, Agent, or Firm* — Kauth, Pomeroy, Peck & Bailey LLP

(57) ABSTRACT

A variety of rose plant of the shrub class, named 'AUStobias'. The 'AUStobias' rose is a plant suitable for repeat flowering production having flowers with buds that start as rounded cups with larger outer petals, enclosing numerous smaller petals within, and that open into perfect rose pink rosette-shaped flowers, with the outer petals forming a perfectly-rounded rim in the form of a saucer. The plant habit of the rose is relatively upright but quite bushy and compact. Initially the fragrance of the flowers is soft myrrh, and as the flower ages it becomes more fruity with a distinct clove character.

1 Drawing Sheet

Classification: The present invention relates to a new *Rosa hybrida* shrub.

Variety denomination: The new plant has the varietal denomination 'AUStobias.'

CROSS-REFERENCE TO RELATED APPLICATIONS

The current application claims priority to a European Community Plant Variety Application No. 2010/2155, filed Oct. 13, 2010, the disclosure of which is incorporated herein by reference.

ORIGIN OF INVENTION

This invention relates to a new and distinct variety of shrub rose plant named 'AUStobias', which was originated by crossing two unnamed, unpatented varieties of *Rosa hybrida.*

BACKGROUND OF THE INVENTION

The primary objective of this breeding was to produce a rose that has superbly-formed rose pink flowers, with buds that start as rounded cups with larger outer petals enclosing numerous smaller petals within that open into rosette-shaped flowers having outer petals that form a perfectly rounded rim in the form of a saucer. The plant habit of this rose is relatively upright but bushy and compact. Finally, the flower would have an initial fragrance of soft myrrh, but that becomes more fruity with a distinct clove character as the flower ages.

SUMMARY OF THE INVENTION

Among the features which distinguish the new variety from others presently available and commercial rose cultivars known to the inventor is the following combination of characteristics: perfect rosette-shaped flowers, flowers having a clear rose pink color, a plant growth that is relatively upright but quite bushy and compact, and a fragrance of myrrh developing fruity with clove as it ages.

Asexual reproduction of the new variety by budding as performed outdoors at Bowling Green Lane in Albrighton, Britain shows that the foregoing and other distinguishing characteristics come true to form and are established and transmitted through succeeding asexual propagations. 'AUStobias' may be asexually propagated by budding. The budding successfully occurred on the plant/rootstock *Rosa* cv. 'Dr. Huey' in the United States, and *Rosa dumetorum* cv. 'Laxa' for the observed plants in the UK.

COMPARISON WITH PARENTS

The new rose may be distinguished from its seed parent, by the following combination of characteristics: whereas the seed parent has yellow, cupped flowers with taller broader growth, 'AUStobias' has pink, rosette-shaped flowers with a compact growth.

The new variety may be distinguished from its pollen parent, by the following combination of characteristics: whereas the pollen parent forms single pink flowers, 'AUStobias' produces double rose pink flowers.

COMPARISON WITH THE CLOSEST COMMERCIALLY AVAILABLE CULTIVAR

The closest commercially available cultivar to the new variety is the 'AUSglisten' (U.S. Plant Pat. No. 8,761). The new rose may be distinguished from the 'AUSglisten' variety by the following combination of characteristics: the 'AUStobias' produces blooms that are a little larger and rosette-shaped with around 80 petals, while 'AUSglisten' has blooms that are smaller and quartered with around 57 petals. 'AUSglisten has a medium old rose perfume compared with the 'AUStobias' myrrh perfume, which turns fruity with clove as it ages.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 1 year-old rose plants of the new variety grown outdoors in Albrighton, Britain in the month of August. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2 cm long and 1.8 cm in diameter when the petals start to unfurl.

*Form*.—The bud form is globular.

*Color*.—When sepals first divide, the bud color is red RHS 39B with orange RHS 29C. When half blown, the upper sides of the petals are red RHS 51A, and the lower sides of the petals are red RHS 51A.

*Calyx*.—Shape: star-shaped. Length: 5.5 cm. Diameter: 5.5 cm.

*Sepals*.—Arrangement: Regular, opening to a star shape. Color: Upper Surface: yellow-green RHS 144B with a whitish down on the surface. Lower Surface: yellow-green RHS 144B with red RHS 146A. Length: 26 mm. Width: 9 mm. Shape: Lanceolate. Margin: N/A. Surface texture: Upper Surface: Hoary (downy). Lower Surface: Smooth. Number: There are three normally appendaged sepals. There are 2 unappendaged sepals with glandular edges.

*Receptacles*.—Color: green RHS 1438 with some red RHS 47A on some. Shape: funnel. Size: medium, about 11 mm×9 mm. Surface: Smooth.

*Peduncle*.—Length: Medium, averaging about 8 cm. Surface: Glandular. Color: Greyed-red RHS 181B. Strength: Strong.

Blooms:

*Size*.—Medium, average open diameter is about 9 cm.

*Borne*.—Several together 4 to 6 blooms having rounded shape.

*Stems*.—Strength: Strong, average length is about 8 cm. Diameter: 4 mm.

*Form*.—When first open, bloom is cupped. Permanence of bloom: outer petals curl back.

Petalage: Number of petals under normal conditions: 57.

*Color*.—The upper sides of the petals are red-purple RHS 63D. The reverse sides of the petals are red-purple RHS 63D. The base of the petals has a medium yellow spot RHS 9D.

*Variegations*.—N/A.

*Discoloration*.—The general tonality at the end of the first day is red-purple RHS 63D, and at the end of the third day is red-purple RHS 63D.

*Fragrance*.—Moderate. Character of fragrance: Myrrh, developing fruity with clove character.

Petals:

*Texture*.—Smooth.

*Size*.—Width: Inner petal 25 mm, outer petal 45 mm. Length: Inner petal 15 mm, outer petal 30 mm.

*Surface*.—Smooth.

*Shape*.—Obovate.

*Margin*.—Undulating, with some petals notched and some entire.

*Apex shape*.—Rounded but undulating, with some petals that are notched.

*Base shape*.—Pointed.

*Form*.—Slightly incurved.

*Arrangement*.—Imbricated.

*Petaloids*.—Number: Few (between 1 and 3). Color: red-purple RHS. 63D. Length: 12 mm. Width: 5 mm. Shape: Elliptic, but curled. Margin: Irregular.

*Persistence*.—Petals drop off cleanly before drying.

*Lastingness*.—On the plant: Fair, about 8 days. As a cut flower: Not tested.

Reproductive parts:

*Stamens*.—Number: 80. Length: 1 cm.

*Anthers*.—Length: 2 mm. Color: yellow-orange RHS 16B. Arrangement: Regular around styles.

*Filaments*.—Color: predominately red-purple RHS 58A, with a few being yellow-orange RHS 16B. Length: 9 mm.

*Pollen*.—Color: yellow-orange RHS 16A.

*Pistils*.—Number: 40. Length: 7 mm.

*Styles*.—Color: red-purple RHS 58A. Length: 5 mm.

*Stigmas*.—Color: red-purple RHS 58A. Length: 2-3 mm. Note: in the center of the reddish stigma and style above, and in addition to them, there are some other pistils which are a green-white RHS 157C.

*Hips*.—None Observed.

PLANT CHARACTERISTICS

Plant form: Shrub.

Plant growth: Quite upright, but compact and bushy.

Age to maturity: Two years.

Mature plant: Height: 90 cm. Width: 90 cm.

Rootstock: *Rosa* cv. 'Dr. Huey' in the United States, *Rosa dumetorum* cv. 'Laxa' for the observed plants in the UK.

Foliage:

*Number*.—Leaflets on normal mid-stem leaves is: 5 (including terminal leaflet).

*Size*.—Large, about 17 cm long×12 cm wide.

*Quantity*.—Normal. Number of leaves per flowering stem is: 10.

*Color*.—New foliage: Upper side: greyed-purple RHS 185A. Lower side: greyed-purple RHS 185A. Old foliage: Upper side: green RHS 137A. Lower side: green RHS 137A.

Leaflets:

*Size*.—About 7 cm long×4.8 cm wide.

*Shape*.—Pointed oval.

*Base shape*.—Rounded.

*Apex shape*.—Acuminate.

*Texture*.—Leathery.

*Edge*.—Serrated.

*Serrations*.—Single.

*Petiole*.—Color: yellow-green RHS 146B. Length: 4 cm. Width: 2 mm. Surface Texture: Smooth.

*Petiole rachis*.—Color: yellow-green RHS 146B. Underside: with prickles.

*Stipules*.—Length: 2.6 cm, glandular. Color: yellow-green RHS 146B.

*Auricle*.—Shape: Strap-shaped. Length: 1 cm. Width: 2 mm. Color: yellow-green RHS 146B.

*Vein color*.—As leaf color.

*Venation pattern*.—Reticulate.

Wood:

*New wood*.—Color: greyed-purple RHS 183A. Bark: Smooth.

*Old wood*.—Color: yellow-green RHS 144A overlaid with greyed-purple RHS 183A. Bark: Smooth.

Branching habit:

*Number*.—6.

*Lateral branch dimensions*.—Length: 16 cm. Width: 6 mm.

Stems:

*Mature stem*.—Length: 70 cm. Diameter: 7 mm.

*Internode distance*.—4 cm. The above measurements are all variable, depending on growing conditions in a season.

*Stem pubescence present*.—No.

Prickles:

*Quantity*.—On main canes from base: Ordinary. Number per stem length: 11 per 10 cm. On laterals from main canes: Ordinary. Number per stem length: 8 per 10 cm.

*Form*.—Deep concave.

*Length*.—10 mm.

*Color when young*.—Red-purple RHS 59A.

*Color when mature*.—Brown RHS 200B.

Small prickles:

*Quantity*.—Main stalk: None. Laterals: None.

Disease resistance:

*Mildew*.—Resistant.

*Blackspot*.—Resistant.

*Rust*.—Resistant.

Pest resistance: Not tested.

Winter hardiness: Not tested.

Growing conditions: Normal.

What is claimed is:

1. A new and distinct variety of rose plant of the shrub class suitable for repeat flower production, substantially as herein shown and described.

* * * * *

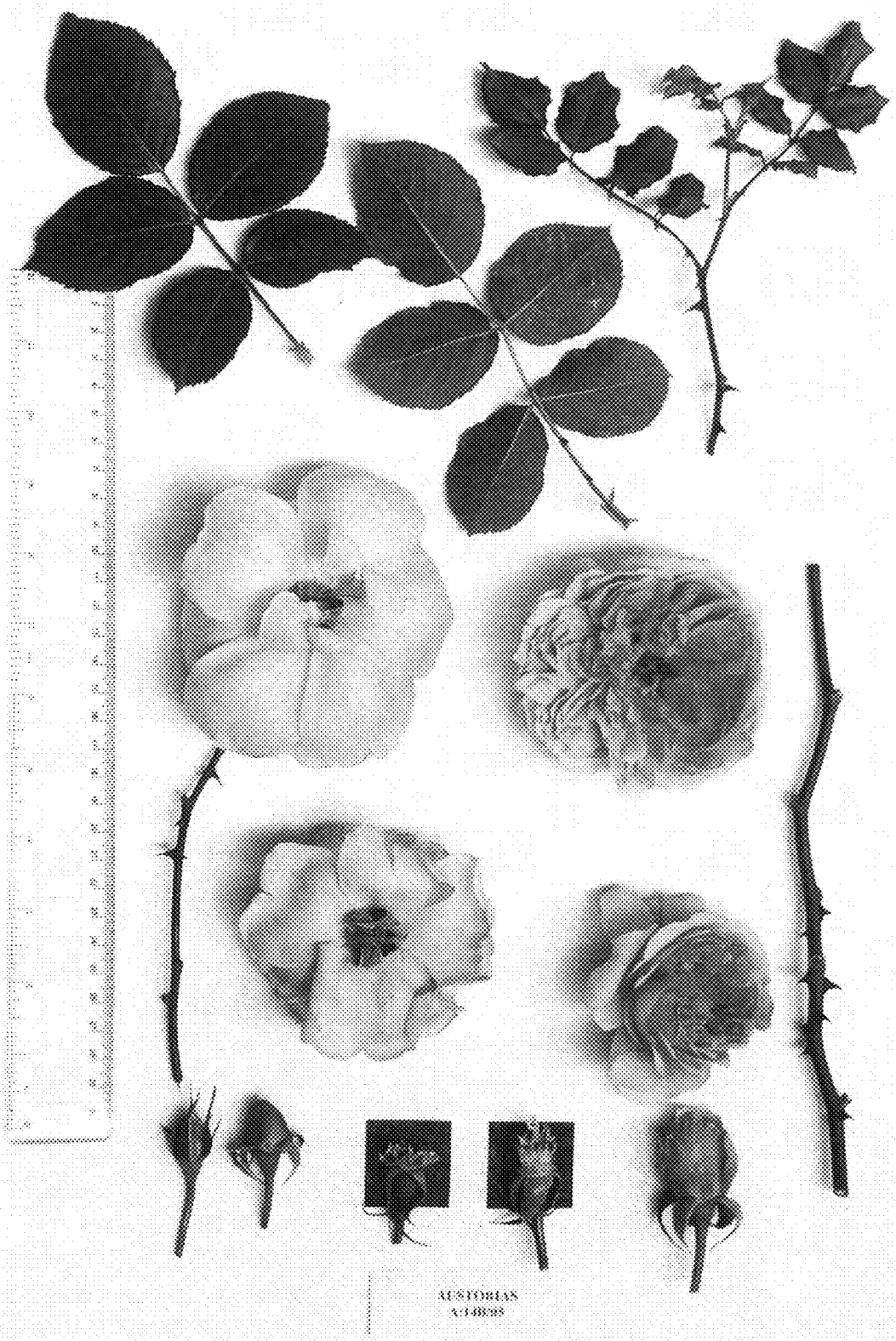
AUSTOBIAS
A-3-BE98